United States Patent

Nohira et al.

Patent Number: 6,028,217
Date of Patent: Feb. 22, 2000

[54] OPTICALLY ACTIVE SALTS OF 2-HYDROXYMETHYL-3-PHENYLPROPIONIC ACID WITH CIS-1-AMINO-2-INDANOL, α-METHYLBENZYLAMINE, OR 3-METHYL-2-PHENYL-1-BUTYLAMINE

[75] Inventors: Hiroyuki Nohira, Urawa; Takayuki Suzuki, Kawasaki; Takayuki Hamada, Kawasaki; Kunisuke Izawa, Kawasaki, all of Japan

[73] Assignee: Ajinomoto Co., Inc., Tokyo, Japan

[21] Appl. No.: 09/166,124

[22] Filed: Oct. 5, 1998

[30] Foreign Application Priority Data

Oct. 3, 1997 [JP] Japan ................................. 9-270680

[51] Int. Cl.$^7$ ................................................. C07B 55/00
[52] U.S. Cl. .................................................. 562/401
[58] Field of Search ............................... 562/401

[56] References Cited

FOREIGN PATENT DOCUMENTS 0 329 156  8/1989  European Pat. Off. .
WO 97 29086  8/1997  WIPO .

*Primary Examiner*—Gary Geist
*Assistant Examiner*—Robert W. Deemie
*Attorney, Agent, or Firm*—Oblon, Spivak, McClelland, Maier & Neustadt, P.C.

[57] ABSTRACT

A compound selected from the group consisting of
(a) optically active 2-hydroxymethyl-3-phenylpropionic acid cis-1-amino-2-indanol salt,
(b) optically active 2-hydroxymethyl-3-phenylpropionic acid α-methylbenzylamine salt,
(c) optically active 2-hydroxymethyl-3-phenylpropionic acid 3-methyl-2-phenyl-1-butylamine salt,
(d) a salt of (S)-2-hydroxymethyl-3-phenylpropionic acid with (1R, 2S)-(+)-cis-1-amino-2-indanol,
(e) a salt of (R)-2-hydroxymethyl-3-phenylpropionic acid with (1S, 2R)-(−)-cis-1-amino-2-indanol,
(f) a salt of (R)-2-hydroxymethyl-3-phenylpropionic acid with (S)-(−)-α-methylbenzylamine,
(g) a salt of (S)-2-hydroxymethyl-3-phenylpropionic acid with (R)-(+)-α-methylbenzylamine,
(h) a salt of (S)-2-hydroxymethyl-3-phenylpropionic acid with (S)-(−)-3-methyl-2-phenyl-1-butylamine, and
(i) a salt of (R)-2-hydroxymethyl-3-phenylpropionic acid with (R)-(+)-3-methyl-2-phenyl-1-butylamine.

10 Claims, No Drawings

OPTICALLY ACTIVE SALTS OF 2-HYDROXYMETHYL-3-PHENYLPROPIONIC ACID WITH CIS-1-AMINO-2-INDANOL, α-METHYLBENZYLAMINE, OR 3-METHYL-2-PHENYL-1-BUTYLAMINE

TECHNICAL FIELD

The present invention relates to a process for optically active 2-hydroxymethyl-3-phenylpropionic acid from (RS)-2-hydroxymethyl-3-phenylpropionic acid by a method of optical resolution and to new substances optically active 2-hydroxymethyl-3-phenylpropionic acid•amine salts which are useful as intermediates for the preparation of the optically active 2-hydroxymethyl-3-phenylpropionic acid.

PRIOR ART

It is known that optically active 2-hydroxymethyl-3-phenylpropionic acid may be employed as an important intermediate for renin inhibitor (J. Med. Chem. 31, 1839 (1988), WO91/16031) or for enkephalinase inhibitor (Japanese Patent Application Kokai (laid-open) Nos. 161/1990 and 59606/1996).

A number of methods have been known for preparing optically active 2-hydroxymethyl-3-phenylpropionic acid as shown below.

That is, there has been proposed a process for preparing optically active 2-hydroxymethyl-3-phenylpropionic acid wherein ① 2-benzyl-1,3-propanediol is subjected to asymmetric esterification with lipase in the presence of vinyl acetate or alternatively ② 2-(acetoxymethyl)-3-phenylpropyl acetate is subjected to asymmetric hydrolysis with lipase, and in either case the formed optically active 2-benzyl-3-hydroxypropyl acetate is oxidized with chromic acid and is subjected to deacetylation [Tetrahedron Lett. 31, 1601 (1990), Liebigs Ann. Chem. 957 (1989)]. However, these processes cause a problem to be performed on industrial scale because of necessity of using toxic chromic acid for oxidation of the alcohol formed by the enzyme reaction to the carboxylic acid. Also, ③ a process is known for preparing optically active 2-hydroxymethyl-3-phenylpropionic acid wherein (4S)-4-(1-methylethyl)-2-oxazolidinone is reacted with a mixture of n-butyllithium and 3-phenylpropionyl chloride to yield phenylpropionylamide, which is reacted with lithiumdiisopropylamide and the resulting enolate is reacted with benzyl bromomethyl ether for asymmetric alkylation, and the obtained product is converted into optically active 2-hydroxymethyl-3-phenylpropionic acid through the additional two steps [Chem. Lett. 505 (1990)]. However, this process is not said to be industrially feasible one because it involves many steps, the use of expensive n-butyllithium and lithiumdiisopropylamide and the need of the low temperature for the reaction. ④ A process is also known for preparing optically active 2-hydroxymethyl-3-phenylpropionic acid wherein (S)-2-isocyano-3-phenylpropyl formate which may be prepared from L-phenylalanine through three steps is inversed by heating at high temperature to form (R)-2-benzyl-3-(formyloxy) propionitrile, which is subjected to hydrolysis [Chem. Ber. 123, 635 (1990)]. However, this process is not suitable for industrial mass—production because higher temperature than 500° C. is required for inversion. Also, a process is known for synthesizing ethyl ester of the optically active 2-hydroxymethyl-3-phenylpropionic acid wherein ethyl ester of α-formyl-β-phenylpropionic acid is reduced to ethyl ester of (R)-2-benzyl-3-hydroxypropionic acid by microbiological fermentation (Japanese Patent Application Kokai (laid-open) No. 199389/1985). This process involves with problem that the optical purity of the compound prepared by the enzyme reaction is not so high.

SUMMARY OF THE INVENTION

An object of the present invention is to provide a method wherein an optical resolution of (RS)-2-hydroxymethyl-3-phenylpropionic acid may be accomplished by simple and convenient procedures.

Another object of the present invention is to provide optically active 2-hydroxymethyl-3-phenylpropionic acid•amine salts which are useful as intermediates for preparing the optically active 2-hydroxymethyl-3-phenylpropionic acid.

According to the present invention, certain class of optically active amines which may be easily recovered and reused and both the R- and S-enantiomers of which are available are used as resolving agents for (RS)-2-hydroxymethyl-3-phenylpropionic acid, whereby there may be obtained new substances optically active 2-hydroxymethyl-3-phenylpropionic acid•amine salts which are useful as intermediates for preparing the optically active 2-hydroxymethyl-3-phenylpropionic acid. The desired optically active 2-hydroxymethyl-3-phenylpropionic acid may be efficiently obtained by decomposing said salt.

DETAILED EXPLANATION OF THE INVENTION

As a result of having investigated in order to achieve the above objects, the present inventors have found that (RS)-2-hydroxymethyl-3-phenylpropionic acid may be resolved into its optically active components in high resolution efficiency by employing as resolving agent certain class of optically active amines which are readily available by chemical technics and the optically active amines used for the resolution may be recovered in high yield, and therefore this method employing the optically active amine resolving agent is an industrially advantageous optical resolution. The present invention is based on the above finding.

That is, the present invention is a process for preparing optically active 2-hydroxymethyl-3-phenylpropionic acid which comprises resolving (RS)-2-hydroxymethyl-3-phenylpropionic acid using as resolving agent an optically active amine selected from the group consisting of optically active cis-1-amino-2-indanol, optically active α-methylbenzylamine and optically active 3-methyl-2-phenyl-1-butylamine.

Also, the present invention relates to new substances optically active 2-hydroxymethyl-3-phenylpropionic acid·cis-1-amino-2-indanol salt, optically active 2-hydroxymethyl-3-phenylpropionic acid·α-methylbenzylamine salt and optically active 2-hydroxymethyl-3-phenylpropionic acid·3-methyl-2-phenyl-1-butylamine salt.

According to the present invention, optically active 2-hydroxymethyl-3-phenylpropionic acid may be obtained by reacting (RS)-2-hydroxymethyl-3-phenylpropionic acid with one of the three optically active amines specified in the above in a suitable solvent to form two diastereomeric salts, separating the less soluble of diastereomeric salt by fractional crystallization utilizing the difference in solubility between the two diastereomeric salts and decomposing the separated diastereomeric salt with an alkali or acid.

(RS)-2-hydroxymethyl-3-phenylpropionic acid which may be employed as the starting material in the present invention may be prepared by the following known methods. For example, it may be synthesized by a process starting with Meldrum's acid which is treated with benzaldehyde and borane triethylamine complex to convert into benzyl Meldrum's acid, which is reacted with benzyl alcohol and the resulting monobenzyl ester of α-benzyl malonic acid is reduced with lithium aluminum hydride to yield 2-hydroxymethyl-3-phenylpropionic acid (WO 92/09297). It may also be synthesized by a process wherein hydrocinnamic acid is treated with lithium diisopropylamide and followed by reaction with gaseous formaldehyde [J. Med. Chem. 35, 1472 (1992)].

It is known that methyl (RS)-2-benzyl-3-hydroxypropionate may be prepared by a process wherein β-propiolactone is cleaved by reaction with methanol in the presence of triethylamine to form methyl 3-hydroxypropionate, which is reacted with lithium diisopropylamide and benzyl bromide for introduction of benzyl group to the α-position (J. Med. Chem. 36, 4015 (1993)]. It is also known that ethyl 2-benzyl-3-hydroxypropionate may be prepared by reacting ethyl α-hydroxymethyl acrylate with diphenylcupper magnesium bromide for conjugate addition of phenyl group [J. Organometallic Chem. 308, C27 (1986)].

As (RS)-2-hydroxymethyl-3-phenylpropionic acid which may be employed in the present invention, in addition to complete racemic form consisting of equal amounts of R- and S-forms, a mixture containing an excess of either enantiomer may be employed.

Optically active cis-1-amino-2-indanol, optically active α-methylbenzylamine and optically active 3-methyl-2-phenyl-1-buthylamine which may be employed as resolving agent in the present invention show a good resolution efficiency toward (RS)-2-hydroxymethyl-3-phenylpropionic acid as demonstrated by the examples described later. Contrary thereto, even if similar optically active amines are 1-(4-tolyl)ethylamine, erythro-2-amino-1,2-diphenylethanol, cis-2-benzylaminocyclohexanemethanol, 1-(1-naphtyl)ethylamine, 1-phenyl-2-(p-tolyl)ethylamine, 2-amino-1-butanol, 1-aminotetralin, 2-amino-3-phenyl-1-propanol, 2-isopropylamino-3-phenyl-1-propanol and phenylalanine amide, they are not suitable for use as the resolving agents because their resolution efficiency is as low as half to one eighth as compared with that of the optically active amine resolving agent involving in the present invention. The specificity based on the optically active amine resolving agent involved in the present invention has been at the first time found as a result of the present inventors' investigation.

Since the above optically active amines which may be employed in the present invention may be prepared by the synthetic technics, both the enantiomers are readily available as commercial products unlike the naturally occurring optically active amines such as brucine and cinchonine. Accordingly, they have the advantage of being able to use properly depending on the optically active form required for 2-hydroxymethyl-3-phenylpropionic acid.

Furthermore, the optically active amines for use in the present invention is very stable so that they do not undergo decomposition and racemization during the resolution and recovery procedures.

As the solvent for use in the present invention it is not particularly restricted so long as it is a neutral solvent such as water, alcohol (e.g. ethanol or isopropanol), acetate (e.g. ethyl acetate or isopropyl acetate), ketone (e.g. acetone, methyl ethyl ketone or methyl isobutyl ketone), nitrile (e.g. acetonitrile), aromatic hydrocarbone (e.g. toluene or xylene), dimethylformamide or ether (e.g. tetrahydrofuran or methyl tertiary butyl ether). Of these solvents, isopropanol, ethanol and methyl isobutyl ketone are preferred. Also, these solvents may be used singly or as a mixture of two or more of being miscible each other.

Although the amount used of the solvent may be varied depending on the kinds of the optically active amine and the solvent to be used, it is usually used in amounts of 3~50 ml per gram of the combined amount of (RS)-2-hydroxymethyl-3-phenylpropionic acid and the optically active amine used.

As to the mixture ratio of (RS)-2-hydroxymethyl-3-phenylpropionic acid to the optically active amine, although there is not involved with any problems if the latter may be used in the range of 0.3~1.5 mol per mol of the former, usually the reaction of the optically active amine with (RS)-2- hydroxymethyl -3-phenylpropionic acid is conducted in an equal molar ratio.

For fractional crystallization of the less soluble of diastereomeric salt, (RS)-2-hydroxymethyl-3-phenylpropionic acid and the optically active amine may be added to the solvent as above-stated simultaneously or separately. In this case, it is recommended that both the (RS)-2-hydroxymethyl-3-phenylpropionic acid and the optically active amine are once dissolved in the solvent in order to obtain the diastereomeric salt having high optical purity. For this purpose, there may be applied a method wherein both the reactants are dissolved in the solvent at dilute concentration and the resultant solution is concentrated to crystallize the diastereomeric salt, or a method wherein they are dissolved in the solvent under heating and subsequently the solution is cooled to crystallize the salt. Alternatively there may be applied a method wherein a solvent capable of lowering the solubility of the diastereomeric salt is added to the above solution, thereby the salt is crystallized out.

The less soluble of diastereomeric salt crystallized out is separable from another more soluble of diastereomeric salt by the conventional solid-liquid separation procedures such as filtration and centrifugation.

The means for decomposing the diastereomeric salt are optional. The diastereomeric salt may be decomposed with an acid or alkali to the desired optically active 2-hydroxymethyl-3-phenylpropionic acid and the raw material optically active amine. More specifically, the diastereomeric salt separated by fractional crystallization is decomposed with an aqueous acidic solution such as hydrochrolic acid and the optically active 2-hydroxymethyl-3-phenylpropionic acid may be obtained by extracting with an organic solvent capable of forming phase separation with water such as ethyl acetate, toluene, dichloromethane or methyl isobutyl ketone. The aqueous layer containing the optically active amine is made alkaline by the addition of an alkali such as sodium hydroxide and the optically active amine may be recovered by the crystallization and separation procedures. Alternatively, the optically active amine may be recovered from the aqueous layer by extraction with a suitable organic solvent such as ethyl acetate, toluene, dichloromethane or methyl isobutyl ketone. The optically active amine thus recovered may be reused for the optical resolution.

The optically active 2-hydroxymethyl-3-phenylpropionic acid obtained according to the process of the present invention may also be used as the preferable resolving agent for RS-cis-1-amino-2-indanol, RS-α-methylbenzylamine and RS-3-methyl-2-phenyl-1-butylamine.

The present invention will be explained in more details with reference to the following examples.

EXAMPLE 1

<Method of assaying the optical purity>

The diastereomeric salt of 2-hydroxymethyl-3-phenylpropinic acid with the optically active amine which was obtained by the optical resolution and crystallization was decomposed by the method shown below to 2-hydroxymethyl-3-phenylpropionic acid and an optically active amine. The enatiomeric excess (ee) of the released acid was measured by chiral HPLC where it was calculated from the ratio of its area to that of the optically active acid developed on the column.

Specifically speaking, the salt obtained by the optical resolution and crystallization was acidified by the addition of 1 M hydrochrolic acid to effect the decomposition. The liberated 2-hydroxymethyl-3-phenylpropionic acid was extracted with ethyl acetate. The assay of the optical purity was conducted with respect to the ethyl acetate layer with an optically active HPLC.

<Measuring condition of HPLC>

Column: DAICEL CHIRALCEL OD-H (4.6×250 mm) (a product of DAICEL CHEMICAL INDUSTRIES, LTD.)

Mobile phase: Hexane/2-propanol/trifluoroacetic acid=95/5/0.1

Flow rate: 1.0/min.

Detection: UV 210 nm

<Calculating formula>

The yield of salt=[(the amount expressed in mol unit of the obtained salt)/(the amount expressed in mol unit of 2-hydroxymethyl-3-phenylpropionic acid used)]×2× 100 (%)

The obtained salt was regarded as the equal molar salt of 2-hydroxymethyl-3-phenylpropionic acid and amine and its yield was calculated based on one of the two optically active forms in the 2-hydroxymethyl-3-phenylpropionic acid.

Resolution efficiency=(optical purity×yield of salt)/100 (%)

EXAMPLE 2

(RS)-2-hydroxymethyl-3-phenylpropionic acid and the optically active amine shown in table 1 were admixed in an equal molar amounts and the mixture was dissolved in the solvent shown in table 1 under heating. The resultant solution was slowly cooled to the room temperature. The precipitated crystals were separated with a suction filter. The separated salt or the salt obtained by concentrating the mother liquor was subjected to decomposition according to the similar manner as in Example 1 and the optical purity of the liberated 2-hydroxymethyl-3-phenylpropionic acid was assayed with a HPLC.

TABLE 1

| | | Resolving Agent | Solvent | Yield of Salt (%) | M.P. of Salt (° C.) | Optical Purity (% ee) | Resolution Efficiency (%) |
|---|---|---|---|---|---|---|---|
| Ex. No. | 3 | (+) cis-AI | Isopropanol | 86.0 | 141 ~ 145 | 79.2 | 68.1 |
| | 6 | (+) cis-AI | Methyl iso-butyl ketone | 85.1 | 142 ~ 145 | 97.9 | 83.3 |
| | 7 | (−) MBA | Water | 51.8 | 144 ~ 146 | 96.6 | 50.0 |
| | 8 | (−) MBA | Water | 40.3 | 143 ~ 145 | 89.7 | 36.1 |
| | 9 | (−) PBA | Water | 75.8 | 139 ~ 140 | 96.9 | 73.5 |
| Control | | (−) TEA | Ethyl acetate | 147.7 | 114 ~ 119 | 20.4 | 9.7 |
| | | | (Mother liquor) | 47.6 | 102 ~ 109 | | |
| | | (+) ADPE | Methanol | 83.7 | | | |
| | | | (Mother liquor) | 119.0 | 167 ~ 169 | 12.8 | 15.2 |
| | | (−) cis-Am | Methanol | 37.5 | 128 ~ 132 | 55.3 | 20.7 |
| | | (−) NEA | Ethanol/Ethyl Acetate (1/4) | 87.6 | 135 ~ 147 | 37.8 | 33.1 |
| | | (+) PTE | Methanol | 122.0 | 148 ~ 152 | 4.2 | 2.9 |
| | | | (Mother liquor) | 70.0 | 138 ~ 144 | | |
| | | (+) 2AB | Ethyl acetate | 118.0 | 89 ~ 91.5 | 4.3 | 2.9 |
| | | | (Mother liquor) | 67.0 | 65 ~ 67 | | |
| | | (−) 1AT | 95% ethanol | 118.0 | 156 ~ 165 | 4.5 | 3.5 |
| | | | (Mother liquor) | 80.5 | 148 ~ 159 | | |
| | | (S) APP | Isopropanol | 16.6 | 92 ~ 102 | 42.2 | 7.0 |
| | | (S) IPAPP | Isopropanol | 125.2 | 120 ~ 132 | 28.0 | 35.1 |
| | | (S) PA | Methyl iso-butyl ketone | 130.8 | 118 ~ 122 | 16.2 | 21.2 |

Note cis-AI: cis-1-amino-2-indanol

MBA: α-methylbenzylamine

PBA: 3-methyl-2-phenyl-1-butylamine

TEA: 1-(4-tolyl)ethylamine

ADPE: erythro-2-amino-1,2-diphenylethanol cis-Am: cis-2-benzylaminocyclohexanemethanol NEA: 1-(1-naphtyl)ethylamine PTE: 1-phenyl-2-(p-tolyl)ethylamine 2AB: 2-amino-1-butanol 1AT: 1-aminotetralin APP: 2-amino-3-phenyl-1-propanol IPAPP: 2-isopropylamino-3-phenyl-1-propanol PA: phenylalanine amide

EXAMPLE 3

8.28 Grams (55.5 mmol) of (IR, 2S)-(+)-cis-1-amino-2-indanol was mixed with 10.0 g (55.5 mmol) of (RS)-2-hydroxymethyl-3-phenylpropionic acid and the mixture was dissolved in 150 ml of isopropanol by heating at 70° C. under stirring. And thereafter the resultant solution was slowly cooled to 30° C. over a period of 8 hours. The precipitated crystals were filtrated under suction, washed with a small amount of isopropanol and dried under reduced pressure. There were obtained 7.86 g of the crystals. The yield of salt was 86.0%. The salt was decomposed according to the similar manner as in Example 1. There was obtained 4.09 g of (S)-2-hydroxymethyl-3-phenylpropionic acid having 79.2% ee of the optical purity. The resolution efficiency was 68.1%.

EXAMPLE 4

311 Mg (2.085 mmol) of (1R, 2S) - (+)-cis-1-amino-2-indanol was mixed with 500.0 mg (2.775 mmol) of (RS)-2-hydroxymethyl-3-phenylpropionic acid and the mixture was dissolved in 8 ml of isopropanol by heating at 70° C. under stirring. And thereafter the solution was slowly cooled on standing and finally in an ice bath. The precipitated crystals were filtrated under suction, washed with a small amount of isopropanol and dried under reduced pressure. There was obtained 361.1 mg of the crystals. The yield of salt was 79.0%. The salt was decomposed according to the similar manner as in Example 1. There was obtained 188 mg of (S)-2-hydroxymethyl-3-phenylpropionic acid having 95.0% ee of the optical purity. The resolution efficiency was 75.1%.

EXAMPLE 5

196.9 Mg (1.32 mmol) of (1R, 2S) - (+)-cis-1-amino-2-indanol was mixed with 500.3 mg (2.776 mmol) of (RS)-2-hydroxymethyl-3-phenylpropionic acid and the mixture was dissolved in 5 ml of isopropanol by heating at 75° C. under stirring. And thereafter the resultant solution was slowly cooled on standing and finally in an ice bath. The precipitated crystals were filtrated under suction, washed with a small amount of isopropanol and dried under reduced pressure. There was obtained 304 mg of the crystals. The yield of salt was 66.4%. The salt was decomposed according to the similar manner as in Example 1. There was obtained 158 mg of (S)-2-hydroxymethyl-3-phenylpropionic acid having 96.6% ee of the optical purity. The resolution efficiency was 64.1 %.

EXAMPLE 6

393.8 Mg (2.64 mmol) of (1R, 2S)-(+)-cis-1-amino-2-indanol was mixed with 502.4 mg (2.788 mmol) of (RS)-2-hydroxymethyl-3-phenylpropionic acid and the mixture was dissolved in 15 ml of 4-methyl-2-pentanone by heating to 70° C. under stirring. And thereafter the resultant solution was slowly cooled to the room temperature. The precipitated crystals were filtrated under suction, washed with a small amount of 4-methyl-2-pentanone and dried under reduced pressure. There was obtained 390.7 mg of the crystals. The yield of salt was 85.1%. The salt was decomposed according to the similar manner as in Example 1. There was obtained 203 mg of (S)-2-hydroxymethyl-3-phenylpropionic acid having 97.9% ee of the optical purity. The resolution efficiency was 83.3 %.

EXAMPLE 7

1.0 Ml of water was added to 159.5 mg (1.318 mmol) of (S)-(−)-α-methylbenzylamine and then 361.5 mg (2.008 mmol) of (RS)-2-hydroxymethyl-3-phenylpropionic acid was added thereto and stirred. And thereafter 1.0 ml of 0.7 mol/L aqueous sodium hydroxide solution was added thereto to neutralize and dissolve an excess amount of (RS)-2-hydroxymethyl-3-phenylpropionic acid, and 1.0 ml of water was further added. The resultant mixture was heated to 90° C. under stirring to form a clear solution and thereafter the solution was slowly cooled to the room temperature. The precipitated crystals were filtrated under suction and dried under reduced pressure. There was obtained 177.4 mg of the crystals. The actual yield of salt was 90.1%.

177.4 Mg of the obtained crystals were dissolved in 1.4 ml of water by heating to 90° C. and the resultant solution was slowly cooled to the room temperature. The precipitated crystals were filtrated under suction and dried under reduced pressure. There was obtained 102.0 mg of the crystals. The total yield of salt was 51.8%. The salt was decomposed according to the similar manner as in Example 1. There was obtained 61 mg of (S)-2-hydroxymethyl-3-phenylpropionic acid having 96.6% ee of the optical purity. The resolution efficiency was 50.0%.

EXAMPLE 8

241 Mg (1.32 mmol) of (S)-(−)-α-methylbenzylamine was added to 359 mg (1.99 mmol) of (RS)-2-hydroxymethyl-3-phenylpropionic acid and then 5 ml of methanol was added thereto. The mixture was stirred and concentrated to dryness. To the obtained salt was added 3 ml of water and then heated to 95° C. to form a clear solution. The solution was slowly cooled to the room temperature. The precipitated crystals were filtrated under suction and dried under reduced pressure. There was obtained 295.5 mg of the crystals. The yield of salt was 99.3%.

292.3 Mg of the obtained crystals was dissolved in 2.33 ml of water by heating to 90° C. and the resultant solution was slowly cooled to the room temperature. The precipitated crystals were filtrated under suction and dried under reduced pressure. There was obtained 118.7 mg of the crystals. The yield of salt was 40.3%. The salt was decomposed according to the similar manner as in Example 1. There was obtained 70 mg of (R)-2-hydroxymethyl-3-phenylpropionic acid having 89.7% ee of the optical purity. The resolution efficiency was 36.1

EXAMPLE 9

6.0 Ml of water was added to 312 mg (2.07 mmol) of (S)-(−)-3-methyl-2-phenyl-1-butylamine and then 372 mg (2.07 mmol) of (RS)-2-hydroxymethyl-3-phenylpropionic acid was added thereto and stirred. And thereafter the mixture was heated to 90° C. to form a clear solution. The solution was slowly cooled and at the time that the temperature of the solution reached to 50° C. 2 mg of the separately prepared salt of (S)-2-hydroxymethyl-3-phenylpropionic acid with (S)-(−)-3-methyl-2-phenyl-1-butylamine was added as the seed crystals and allowed to stand at the room temperature for 3 hours and cooled for further 30 minutes in an ice-water bath.

The precipitated crystals were filtrated under suction, washed with a small amount of water and dried under reduced pressure. There was obtained 257 mg (0.78 mmol) of crystals. The yield of salt was 75.8%. The salt was decomposed according to the similar manner as in Example 1. There was obtained 140 mg of (S)-2-hydroxymethyl-3-phenylpropionic acid having 96.9% ee of the optical purity. The resolution efficiency was 73.5%.

Of course, the optical purity of the optically active 2-hydroxymethyl-3-phenylpropionic acid produced by the present process is, preferably, as high as possible. Preferably, the optical purity of the optically active 2-hydroxymethyl-3-phenylpropionic acid is at least 50% e.e., more preferably at least 75% e.e., even more preferably at least 85% e.e., still even more preferably at least 90% e.e, and, most preferably, at least 95% e.e. These ranges include all specific values and subranges therebetween, such as 55%, 60%, 70%, 80% e.e., as well as 96%, 97%, 98%, 99% or 100% e.e.

Likewise, the isolated yield of the separated diastereomeric salt is preferably as high as possible. Preferably, the yield is at least 30%, more preferably at least 50%, even more preferably at least 75%, even more preferably at least 85%, and, most preferably, at least 90%.

It is also preferred that the resolution efficiency, discussed above, be as high as possible. Preferably, the resolution efficiency is at least 30%, more preferably at least 50%, even more preferably at least 75%, even more preferably at least 85%, and, most preferably, at least 90%.

Obviously, numerous modifications and variations of the present invention are possible in light of the above teachings. It is therefore to be understood that within the scope of the appended claims, the invention may be practiced otherwise than as specifically described herein.

Japanese Patent Application Serial No. 270680/1997, filed on Oct. 3, 1997, is incorporated herein by reference in its entirety.

We claim:

1. A compound selected from the group consisting of
    (a) optically active 2-hydroxymethyl-3-phenylpropionic acid cis-1-amino-2-indanol salt,
    (b) optically active 2-hydroxymethyl-3-phenylpropionic acid α-methylbenzylamine salt,
    (c) optically active 2-hydroxymethyl-3-phenylpropionic acid 3-methyl-2-phenyl-1-butylamine salt,
    (d) a salt of (S)-2-hydroxymethyl-3-phenylpropionic acid with (1R, 2S)-(+)-cis-1-amino-2-indanol,
    (e) a salt of (R)-2-hydroxymethyl-3-phenylpropionic acid with (1S, 2R)-(−)-cis-1-amino-2-indanol,
    (f) a salt of (R)-2-hydroxymethyl-3-phenylpropionic acid with (S)-(−)-α-methylbenzylamine,
    (g) a salt of (S)-2-hydroxymethyl-3-phenylpropionic acid with (R)-(+)-α-methylbenzylamine,
    (h) a salt of (S)-2-hydroxymethyl-3-phenylpropionic acid with (S)-(−)-3-methyl-2-phenyl-1-butylamine, and
    (i) a salt of (R)-2-hydroxymethyl-3-phenylpropionic acid with (R)-(+)-3-methyl-2-phenyl-1-butylamine.

2. The compound of claim 1, which is (a).
3. The compound of claim 1, which is (b).
4. The compound of claim 1, which is (c).
5. The compound of claim 1, which is (d).
6. The compound of claim 1, which is (e).
7. The compound of claim 1, which is (f).
8. The compound of claim 1, which is (g).
9. The compound of claim 1, which is (h).
10. The compound of claim 1, which is (i).

* * * * *

UNITED STATES PATENT AND TRADEMARK OFFICE
CERTIFICATE OF CORRECTION

PATENT NO. : 6,028,217
DATED : February 22, 2000
INVENTOR(S) : Hiroyuki Nohira, et al.

It is certified that error appears in the above-identified patent and that said Letters Patent is hereby corrected as shown below:

<u>Column 8,</u>
Line 41, "was 36.1" should read -- was 36.1%. --.

Signed and Sealed this

Twenty fifth Day of September, 2001

Attest:

*Nicholas P. Godici*

NICHOLAS P. GODICI
*Attesting Officer*  *Acting Director of the United States Patent and Trademark Office*